(12) United States Patent
Burba

(10) Patent No.: US 11,561,324 B1
(45) Date of Patent: Jan. 24, 2023

(54) METHODS AND APPARATUS FOR MEASURING GAS FLUX

(71) Applicant: LI-COR, Inc., Lincoln, NE (US)

(72) Inventor: George Burba, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 344 days.

(21) Appl. No.: 17/081,250

(22) Filed: Oct. 27, 2020

(51) Int. Cl.
G01W 1/02 (2006.01)
G01P 5/02 (2006.01)
G01N 33/00 (2006.01)
G01K 13/02 (2021.01)
G01K 13/024 (2021.01)

(52) U.S. Cl.
CPC ............... *G01W 1/02* (2013.01); *G01K 13/02* (2013.01); *G01N 33/0036* (2013.01); *G01P 5/02* (2013.01); *G01K 13/024* (2021.01); *G01W 2201/00* (2013.01)

(58) Field of Classification Search
CPC ....... G01W 1/02; G01W 2201/00; G01P 5/02; G01N 33/0036; G01K 13/02; G01K 13/024
USPC .......................................................... 702/3
See application file for complete search history.

(56) References Cited

U.S. PATENT DOCUMENTS

| 6,317,212 | B1 | 11/2001 | Eckles |
| 6,369,387 | B1 | 4/2002 | Eckles |
| 8,125,626 | B2 | 2/2012 | Furtaw |
| 8,130,379 | B1 | 3/2012 | Burba et al. |
| 10,060,942 | B2 | 8/2018 | Burba et al. |
| 2011/0054803 | A1* | 3/2011 | Burba ............... G01N 21/3504 702/23 |

OTHER PUBLICATIONS

"CPEC200 Closed-Path Eddy-Covariance Flux System," Campbell Scientific, Inc. Publication, Logan, UT, Copyright 2011, 2012, Printed Apr. 2012 (3 pages).
"EC155 CO2 and H2O Closed-Path Gas Analyzer and EC100 Electronics with Optional CSAT3A 3D Sonic Anemometer Revision: Aug. 2011 Instruction Manual," Campbell Scientific, Inc. Publication, Copyright 2010-2011 (63 pages).

(Continued)

*Primary Examiner* — Aditya S Bhat
(74) *Attorney, Agent, or Firm* — Gerald T. Gray; Leydig, Voit & Mayer, Ltd.

(57) ABSTRACT

Systems and methods for measuring gas flux are provided. The method includes obtaining one or more of wind speed data, gas content data, temperature data and humidity data over a period of time, computing a plurality of different gas flux values for said period of time using a corresponding plurality of different flux calculation algorithms, wherein each of the plurality of different flux calculation algorithms uses one, some or all of the measured data types to calculate gas flux values for one or a plurality of sub-periods of said period of time, and for each of the one or the plurality of sub-periods, determining an optimal flux calculation algorithm of the plurality of different flux calculation algorithms based on one or more quality indicators; and outputting, for each of the plurality of sub-periods, one or more optimal flux calculation values corresponding to the optimal flux calculation algorithm for the sub-period.

20 Claims, 6 Drawing Sheets

(56) References Cited

OTHER PUBLICATIONS

Sargent, Steve et al., "Frequency Response of a Low-Power Closed-Path CO2 and H2O Eddy Covariance System," Campbell Scientific, Inc., Logan UT, CPEC200 brochure copyright 2012, 2016 (1 page).
Hendriks, D.M.D et al., "A compact and stable eddy covariance set-up for methane measurements using off-axis integrated cavity output spectroscopy," Atmos. Chem. and Phys., 8, pp. 431-443, 2008.
Bowling, David R. et al., "The use of relaxed eddy accumulation to measure biosphere-atmosphere exchange of isoprene and other biological trace gases," Oecologia, 116(3), pp. 306-315., copyright Springer-Verlag, Sep. 1998.
Zhao, Xiaosong et al., "A comparison of flux variance and surface renewal methods with eddy covariance," IEEE Journal of Selected Topics in Applied Earth Observations and Remote Sensing, vol. 3(3), pp. 345-350, 2010.
Castellvi, F., "Fetch requirements using surface renewal analysis for estimating scalar surface fluxes from measurements in the inertial sublayer," Agricultural and Forest Meteorology 152 (2012) pp. 233-239.
Castellvi, F. et al., "Estimating sensible and latent heat fluxes over rice using surface renewal," Agricultural and Forest Meteorology 139(1-2), pp. 164-169, 2006.
Kyaw, Tha Paw U. et al., "Surface Renewal Analysis: A New Method to Obtain Scalar Fluxes," Agricultural and Forest Meteorology 74, pp. 119-137, 1995.
Castellvi, F. et al., "Surface energy-balance closure over rangeland grass using the eddy covariance method and surface renewal analysis," Agricultural and Forest Meteorology 148 (2008), pp. 1147-1160.
Wilson, Kell B. et al., "A comparison of methods for determining forest evapotranspiration and its components: sap-flow, soil water budget, eddy covariance and catchment water balance," Agricultural and Forest Meteorology 106, pp. 153-168, 2001.
Lavigne, M.B. et al., "Comparing nocturnal eddy covariance measurements to estimates of ecosystem respiration made by scaling chamber measurements at six coniferous boreal sites," Journal of Geophysical Research: Atmospheres, 102(D24), pp. 28977-28985, Dec. 26, 1997.
Liu, S.M. et al., "A comparison of eddy-covariance and large aperture scintillometer measurements with respect to the energy balance closure problem," Hydrology and Earth System Sciences, 15(4), pp. 1291-1306, 2011.
Williams, D.G. et al., "Evapotranspiration components determined by stable isotope, sap flow and eddy covariance techniques," Agricultural and Forest Meteorology 125, pp. 241-258, 2004.

* cited by examiner

FIG. 4

- EC = eddy covariance method
- EC-RR = eddy covariance method rapidly resolved for short-period fluxes and episodic events
- SR = surface renewal method (3 flavors)
- EA = bag-free eddy accumulation method (2 flavors)
- REA = bag-free relaxed eddy accumulation method (2 flavors)
- Size of font indicates if the method is primary, secondary, tertiary, etc.

| | | System Frequency Response in Relation to Frequency of Ambient Turbulent Transport | | |
|---|---|---|---|---|
| | | Faster Instruments | | Slower Instruments |
| | | >5 Hz | 1-5 Hz | <1 Hz |
| Measurement Height Determining Plot Size (Larger plots ↕ Smaller plots) | >2 m | EC<br>EC-RR<br>SR$_{1,2,3}$<br>EA$_{1,2}$<br>REA$_{1,2}$<br>Others | EC<br>EA$_{1,2}$<br>REA$_{1,2}$<br>SR$_{1,2,3}$<br>EC-RR<br>Others | EA$_{1,2}$<br>REA$_{1,2}$<br>EC<br>EC-RR<br>SR$_{1,2,3}$<br>Others |
| | 1-2 m | SR$_{1,2,3}$<br>EC<br>EC-RR<br>EA$_{1,2}$<br>REA$_{1,2}$<br>Others | SR$_{1,2,3}$<br>EC (calibrates SR)<br>EC-RR<br>EA$_{1,2}$<br>REA$_{1,2}$<br>Others | EA$_{1,2}$<br>REA$_{1,2}$<br>SR$_{1,2,3}$<br>EC<br>EC-RR<br>Others |
| | <1 m | SR$_{1,2,3}$<br>EC<br>EC-RR<br>EA$_{1,2}$<br>REA$_{1,2}$<br>Others | SR$_{1,2,3}$<br>EC (calibrates SR)<br>EC-RR<br>EA$_{1,2}$<br>REA$_{1,2}$<br>Others | SR$_{1,2,3}$<br>EA$_{1,2}$<br>REA$_{1,2}$<br>EC<br>EC-RR<br>Others |

METHODS AND APPARATUS FOR MEASURING GAS FLUX

BACKGROUND

The present embodiments relate generally to systems and methods for measuring gas flux, and more particularly to systems and methods for measuring turbulent gas flux and automatically determining an optimal gas flux determination method from among multiple possible gas flux determination protocols.

The increasing concentrations of carbon dioxide and other traces gases (e.g. $H_2O$, $CH_4$, $N_2O$, $NH_3$, etc.) in the atmosphere and the resulting greenhouse effect and climate change have become important topics for scientific research. In order to understand the global carbon balance, it is necessary to determine the rate at which carbon dioxide, other trace gases, and energy exchange between the atmosphere and terrestrial and oceanic ecosystems. The air within a few hundred meters above the earth's surface is mostly turbulent, so that turbulent structures (vortices of variable sizes) called "eddies" are responsible for the vertical transport of most of the gases, including carbon dioxide and water vapor, and also heat and momentum between the surface and the atmosphere. Using various gas flux calculation methods, the rates of such transport can be calculated from simultaneous (often high-frequency) measurements of the vertical component of wind speed, the concentrations of carbon dioxide and water vapor, and the air temperature.

Currently, the main methods for computing turbulent gas flux rates, typically performed from towers, airplanes and other platforms, include Eddy Covariance, Eddy Accumulation, and Relaxed Eddy Accumulation methods.

The Eddy Covariance (EC) method is the most direct and reliable method for gas flux measurements available to date. EC is a dominating method used in most turbulent flux measurements. EC is used as a standard for other turbulent flux measurement methods, and for any atmospheric flux measurement methods. However, EC requires high-speed gas concentration measurements (e.g., 5-10 Hz or more) in addition to the high-speed vertical wind speed measurements (e.g., 5-10 Hz or more).

The Eddy Accumulation (EA) method is theoretically as reliable as EC, and it also requires high-speed vertical wind speed measurements, but it does not require high-speed gas concentration measurements. However, EA does need a highly sophisticated high-speed wind sampling system to distinguish updrafts from downdrafts, and another highly sophisticated high-speed system to sample gas into accumulation bags in proportion to the rates of the updrafts and downdrafts.

The Relaxed Eddy Accumulation (REA) method is a version of EA which does not require sampling in proportion to the rate of the updrafts and downdrafts. However, REA does also require a sophisticated high-speed wind sampling system to distinguish updrafts from downdrafts, while sampling into the accumulation bags is done at a constant flow rate. REA is not able to measure fluxes as reliably as EC or EA due to an empirical parameter required for calculations, but REA may be used for measuring fluxes of gas species for which no high-speed gas measurement devices are available. Both the EA and the REA methods also have built-in measurement uncertainties associated with system configurations and components such as valve systems, sampling delays, tube time delays and attenuation, etc.

A recent, bag-free methodology as described in U.S. Pat. No. 10,060,942, which is incorporated herein by reference in its entirety for all purposes, includes taking high-speed vertical wind speed measurements (e.g., on the order of 5-10 Hz or more) and low-speed gas content (e.g., density or concentration) measurements (e.g., on the order of 5 Hz or less), without the need for the sophisticated and expensive high-speed hardware to separate gas samples (e.g., into accumulation bags) according to updrafts and downdrafts. A time series of high-speed vertical wind speed data is used as a guide to distinguish between updrafts and downdrafts: when vertical wind speed is upward (updraft), the low-speed gas content is recorded into a data structure in one location, or marked with one flag; when vertical wind speed is downward (downdraft), the low-speed gas content is recorded into a different location, or marked with a different flag. Eddy Accumulation or Relaxed Eddy Accumulation computations can be performed using the stored gas content data to determine gas flux. Such gas flux measurements are useful for measuring or estimating heat, water and $CO_2$ exchange as well as methane and other trace gases.

There are also methods based on the slow measurements of gas concentrations at one or more levels, such as gradient, aerodynamic, Bowen ratio, and modeling techniques based on gas concentrations measurements at one or more levels.

However, in present systems, the firmware, processing codes and field operation regiments are generally designed to measure fluxes with only one of the methods.

However, some methods work better in some atmospheric and site conditions and work worse in other conditions, and vice-versa.

Therefore it is desirable to provide systems and methods that overcome the above and other problems.

SUMMARY

Various embodiments advantageously provide systems and methods for measuring gas flux, and more particularly systems, methods and devices for measuring turbulent gas flux using multiple gas flux determination methodologies and determining the optimal gas flux determination methodology (and hence also gas flux values) for a given time period or periods during which measurements were taken.

The present embodiments provide logic for determining and recommending the best method for a given time period, and also for identifying and presenting the best flux results for different periods, which may be calculated using the same method or different methods as determined by the logic. The various embodiments herein provide significant advantages by enabling a single flux station to compute gas fluxes using multiple methods, and also recommend the best flux results for a given time period.

The various embodiments advantageously enable substantially simultaneous, real-time flux calculations using multiple different flux calculations from the same dataset, and providing a recommendation of the best estimate of the flux for each of the plurality of time periods.

According to an embodiment, a method of measuring gas flux and determining an optimal gas flux value from among multiple possible values is provided. The method includes obtaining wind speed data, the wind speed data including a plurality a wind speed measurements measured by a wind speed measurement device over a period of time at a sampling rate of the wind speed measurement device, obtaining gas content data, the gas content data including a plurality of gas content measurements measured by a gas analyzer over substantially the same period of time at a sampling rate of the gas analyzer, and computing a plurality of different gas flux values for the period of time using a corresponding plurality of different flux calculation algorithms. For example, each of the plurality of different flux calculation algorithms may produce one of the corresponding different gas flux values. Each of the plurality of different flux calculation algorithms may use one or both of the wind speed data and the gas content data to calculate gas flux values for a plurality of sub-periods or intervals of the period of time for which measurements were taken. In certain aspects, the method further includes, for each of the plurality of sub-periods or intervals of the period of time, determining an optimal flux calculation algorithm from among the plurality of different flux calculation algorithms based on one or more quality indicators, and outputting or storing, for each of the plurality of sub-periods, one or more optimal flux calculation values corresponding to the optimal flux calculation algorithm as determined for the sub-period.

In certain aspects, the wind speed data may include vertical wind speed data and/or horizontal wind speed data.

In certain aspects, the "period of time," i.e., a period of time during which measurements are taken by both the wind speed measurement device and gas analyzer and/or other environmental parameter detection devices, may be greater than the actual time period during which measurements are actually taken by either device, such that if/when there is a discrepancy or difference of up to a few or several minutes between when the wind speed measurement device measures and the gas analyzer measures, the actual measurements taken fall within the "period of time". In this manner, the algorithms may use values from slightly different shifted timings, all of which may be considered to be within the "period of time." Further, "the substantially same period of time" during which measurements are taken by different devices encompasses the situation where one shifts the measurement time interval of one device by a few seconds or even a few minutes (e.g., <10 min for 60 min period; <1 min for 5 min period) relative to the measurement time interval of another device.

According to certain aspects, the method further includes displaying one or more of: the one or more optimal flux values determined for each of the plurality of sub-periods or time intervals; the flux values computed according to or using a primary flux calculation algorithm, wherein the primary flux calculation algorithm is the flux calculation algorithm having the most number of sub-periods or time intervals being determined as the optimal flux calculation algorithm; and the gas flux values for each of the plurality of sub-periods or intervals computed according to each of the plurality of different flux calculation algorithms.

According to certain aspects, the plurality of different flux calculation algorithms include one or more of an eddy covariance (EC) flux calculation algorithm, an eddy accumulation (EA) flux calculation algorithm, a relaxed eddy accumulation (REA) flux calculation algorithm, a surface renewal (SR) flux calculation algorithm, a gradient flux calculation algorithm, a resistance flux calculation algorithm, an aerodynamic flux calculation algorithm, a Bowen ratio flux calculation algorithm, and an integrated horizontal flux calculation algorithm.

In certain aspects, the one or more quality indicators include parameters selected from the group consisting of environmental parameters and system parameters.

According to certain aspects, the method further includes determining a primary flux calculation algorithm as the flux calculation algorithm having the most number of sub-periods or intervals being determined as the optimal flux calculation algorithm, and for a first sub-period or interval, tuning or calibrating one of the other flux calculation algorithms not determined as the primary flux calculation algorithm based on the computed flux value of the primary flux calculation algorithm for the first sub-period or interval. The first sub-period may (or may not) be a sub-period when the primary algorithm is the optimal algorithm, for example, the first sub-period may be one of the sub-periods where both the primary algorithm and "calibrated" algorithm have a sufficiently reliable flux output.

In certain aspects, for a second sub-period or time interval, wherein the primary flux calculation algorithm either is unable to calculate a gas flux value, or is determined as not being the optimal flux calculation algorithm, the method further includes using the computed flux value of the tuned or calibrated flux calculation algorithm for the second sub-period or interval.

In certain aspects, the method further includes obtaining temperature data, the temperature data including a plurality of temperature measurements measured by a temperature measuring device over substantially the same period of time, and wherein at least one of the plurality of different flux calculation algorithms uses the temperature data when calculating gas flux values for the plurality of sub-periods or intervals.

In certain aspects, the sampling rate of the wind speed measurement device is different than the sampling rate of the gas analyzer.

In certain aspects, one or more or all of the steps of computing, determining and outputting or storing are performed automatically in real-time as the vertical wind speed data and the gas content data are being obtained.

In certain aspects, the method includes obtaining temperature data, the temperature data including a plurality of temperature measurements measured by a temperature measuring device over substantially the same period of time, and wherein at least one of the plurality of different flux calculation algorithms uses the temperature data and the vertical wind speed data to calculate sensible heat flux values for the plurality of sub-periods or intervals.

In certain aspects, the method further includes obtaining temperature data, the temperature data including a plurality of temperature measurements measured by a temperature measuring device over substantially the same period of time, and wherein at least one of the plurality of different flux calculation algorithms uses the temperature data to calculate sensible heat flux values for the plurality of sub-periods or intervals (i.e., without using wind speed data).

In certain aspects, the method further includes obtaining humidity data, the relative humidity data including a plurality of humidity measurements measured by a humidity measuring device over said period of time, and wherein at least one of the plurality of different flux calculation algorithms uses the humidity data to calculate latent heat flux values for the plurality of sub-periods or intervals. In certain aspects, metrics of humidity may include relative humidity, absolute humidity, water vapor concentration, water vapor density, water content, etc.

In certain aspects, the method further includes obtaining gas concentration data, including a plurality of gas concentration measurements measured by a gas concentration measuring device over substantially the same period of time, and wherein at least one of the plurality of different flux calculations uses the gas concentration data to calculate gas flux values for the plurality of sub-periods or intervals.

In certain aspects, the method further includes assigning a quality value or quality indicator to each of the plurality of different flux calculation algorithms used when computing the plurality of different gas flux values for the period of time.

According to another embodiment, a system for measuring gas flux is provided. The system includes a wind speed measurement device configured to obtain wind speed data including a plurality a wind speed measurements obtained over a period of time at a first sampling rate, a gas analyzer configured to obtain gas content data including a plurality of gas content measurements obtained over substantially the same period of time at a second sampling rate, and an intelligence module (e.g., including one or more processors and associated memory) adapted to receive and process the wind speed data and the gas content data. In certain aspects, the intelligence module is configured to automatically: compute a plurality of different gas flux values for the period of time using a corresponding plurality of different flux calculation algorithms, wherein each of the plurality of different flux calculation algorithms uses one or both of the wind speed data and the gas content data to calculate gas flux values for a plurality of sub-periods or intervals of the period of time; for each of the plurality of sub-periods or intervals of the period of time, determine an optimal flux calculation algorithm of the plurality of different flux calculation algorithms based on one or more quality indicators; and output or store, for each of the plurality of sub-periods or intervals, one or more optimal flux calculation values corresponding to the optimal flux calculation algorithm for the sub-period or interval. In certain aspects, the wind speed data may include vertical wind speed data and/or horizontal wind speed data.

According to another embodiment, a method of measuring gas flux is provided that includes obtaining over a period of time one or more of wind speed data, gas content data, temperature data and humidity data, computing a plurality of different gas flux values for said period of time using a plurality of different flux calculation algorithms, wherein each of the plurality of different flux calculation algorithms uses one, some or all of the wind speed data, the gas content data, the temperature data and the humidity data to calculate gas flux values for one or a plurality of sub-periods of said period of time, for each of the one or the plurality of sub-periods of said period of time, determining an optimal flux calculation algorithm of the plurality of different flux calculation algorithms based on one or more quality indicators, and outputting or storing, for each of the plurality of sub-periods, one or more optimal flux calculation values corresponding to the optimal flux calculation algorithm for the sub-period.

In a further embodiment, a non-transitory computer readable medium is provided that stores instructions, which when executed by at least one processor, causes the at least one processor to control operation of system components and/or to implement any data processing method as described herein. Examples of computer readable media include RAM, ROM, CDs, DVDs, ASICs, FPGAs or other circuit elements including memory elements.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWING(S)

FIG. 4 shows one example of an algorithm than can be used to determine primary and secondary methods according to an embodiment.

DETAILED DESCRIPTION

Figure 1:
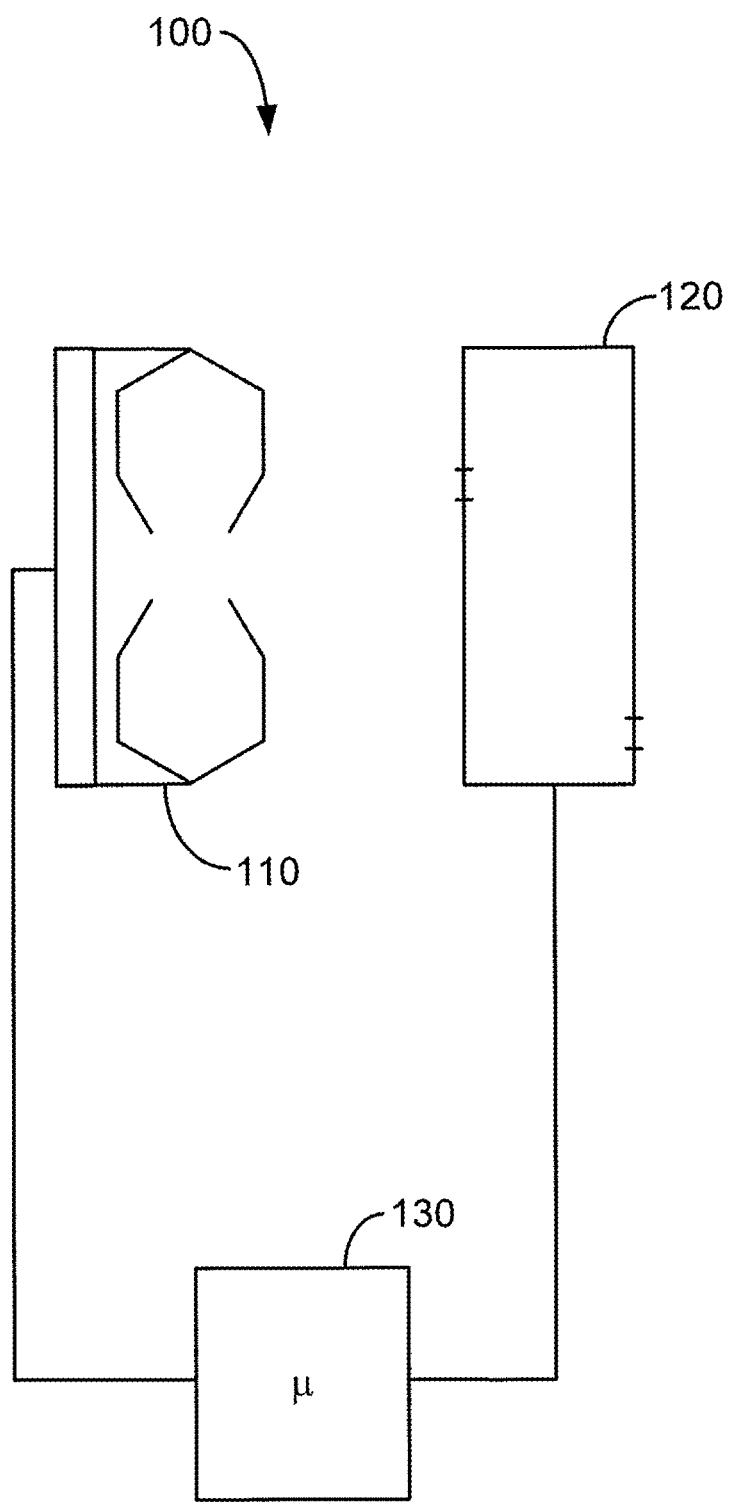
FIG. 1 illustrates a gas flux measurement system 100 according to an embodiment.

Various system and method embodiments are provided for enabling substantially simultaneous, real-time gas flux calculations using multiple different flux determination methods or protocols and using the same dataset, as well as providing a recommendation of the best estimate of the flux for each of a plurality of time periods.

In an embodiment, a station (e.g., system including measurement devices and processing logic and circuitry) computes fluxes by several methods simultaneously, then automatically evaluates and identifies which method may be the best and most reliable 'primary' method (usually Eddy Covariance for larger plots and likely Surface Renewal for smaller plots) for a given time period depending on various system and environmental parameters such as atmospheric conditions, a state of the measurement system, quality control flags and/or various other criteria and statistics.

In some embodiments, the station selects the periods when a primary method has high quality performance (typically indicated by method/equipment quality flags or similar indicators) and uses these periods to tune or "calibrate" one or more secondary methods. The secondary methods may be used to gap-fill the time periods during which the primary method may have had low-quality performance.

Processing software is provided to distinguish between multiple gas flux determination methods, e.g., processing data by the several methods using the received gas flux data (or stored gas flux data), assess the quality of each method using quality and descriptive statistics, and recommend the best flux value for each time period. The gas flux data may include one or more of gas concentration data, directional wind speed data, temperature data, humidity data and other data types as will be described herein and as would be apparent to one skilled in the art.

Accordingly, the present embodiments provide flux measurement systems that can produce flux measurements computed with multiple different methods in a substantially simultaneous fashion (e.g., within the same 5-240 min time periods), select the best method for a specific period, recover other methods for their respective poor periods, present the multitude of results from all methods with descriptive statistics, and also, produce the best estimate of the flux over longer measurement periods regardless of the method or methods used.

Non-limiting examples of gas flux determination methods that can process a dataset acquired by a station include the following:

Eddy Covariance—classical (likely a primary method for regular fluxes most of the time over large plots)

Eddy Covariance—Kowalski/Fratini (likely a primary method for very small fluxes over large plots)

Eddy Covariance—RR (rapidly resolved for very-short-period fluxes and episodic events)

Surface Renewal (e.g., 4 flavors; likely primary method for small plots, night times and/or non-operational anemometer)

Disjunct Eddy Covariance (potential backup method when flux systems a bit too slow for conditions)

Valve and bag-free EA (e.g., 2 flavors; likely primary method for slower analyzers or non-operational pump, potentially useful at night)

Valve and bag-free REA (e.g., 2 flavors; likely primary method for slower analyzers or non-operational pump, potentially useful at night)

Gradient (e.g., backup method when profile is available)

Resistance (e.g., another backup method when profile is available)

Aerodynamic (e.g., another backup method when profile is available)

Bowen ratio (e.g., another backup method when profile is available)

Integrated horizontal flux, and multiple other future methods and modeling techniques.

Various embodiments use multiple gas flux computation paradigms to perform flux computations. Some embodiments use gas flux determination paradigms that use low speed or high-speed hardware to separate gas samples according to updrafts and downdrafts.

Use of the Eddy Covariance (EC) method, for example, is the most direct and reliable method for gas flux measurements available to date. EC is a method used in most turbulent flux measurements. EC is often used as a standard for other turbulent flux measurement methods, and for any atmospheric flux measurement methods. However, EC requires high-speed gas concentration measurements (e.g., 5-10 Hz or more) in addition to the high-speed vertical wind speed measurements (e.g., 5-10 Hz or more). However, high-speed gas concentration measurement devices do not exist for a number of gas species.

Using the traditional Eddy Accumulation (EA) method, for example, turbulent gas flux may be computed as follows:

$$F=C\uparrow W\uparrow - C\downarrow W\downarrow \qquad [1]$$

where F is gas flux, $C\uparrow$ is the averaged gas content of samples accumulated into an updraft bag, $C\downarrow$ is the averaged gas content of samples accumulated into a downdraft bag, $W\uparrow$ is the average speed of updrafts, and $W\downarrow$ is the average speed of downdrafts. In operation, $C\uparrow$ is collected into the updraft bag only during updrafts, and is collected with the sampling flow proportional to the updraft rate. Similarly, $C\downarrow$ is collected into the downdraft bag only during downdrafts, and is collected with the sampling flow proportional to the downdraft rate. Traditionally, EA requires a high-speed device (including valves, solenoids, etc.) and related electronics that need to operate with extremely high-speed and accuracy to distinguish between updrafts and downdrafts, which often change at rate of about 10 Hz (10 times a second) or greater. The high-speed sampling device (such as a pump, or blower and sampling bags) and related electronics should be high-speed and sensitive to be able to sample at a rate proportional to the vertical wind speed, which changes sign very fast, and has generally low magnitudes, e.g., of about 0.01-2.0 m/s.

Using the Relaxed Eddy Accumulation (REA) method, for example, turbulent gas flux may be computed as follows:

$$F=\beta\sigma_w(Q\uparrow - Q\downarrow) \qquad [2]$$

where F is the gas flux, $\beta$ is an empirical coefficient (Katul et al. (1994) uses $\beta=\sigma_w(W\uparrow-W\downarrow)$), $\sigma_w$ is the standard deviation of W, the vertical wind speed over a given period of time, or other similar statistical parameter describing variation (e.g., squared variance, etc.), $Q\uparrow$ is the averaged gas content of samples accumulated into an updraft bag, $Q\downarrow$ is the averaged gas content of samples accumulated into a downdraft bag, $W\uparrow$ is the average speed of updrafts, and $W\downarrow$ is the average speed of downdrafts. In operation, $Q\uparrow$ is collected into the updraft bag only during updrafts, and is collected with the constant sampling flow rate (not proportional to the updraft rate). Similarly, $Q\downarrow$ is collected into the downdraft bag only during downdrafts, and is collected with the constant sampling flow rate (not proportional to the downdraft rate). Traditionally, REA requires a high-speed device (including valves, solenoids, etc.) and related electronics that have to operate with extremely high-speed and accuracy to distinguish between updrafts and downdrafts, which often change at a rate of about 10 Hz (10 times a second) or greater. Also, the coefficient $\beta$ is highly variable and is not always predictable. Nevertheless, the REA method is used much more often than the EA method, likely because the hardware needed is easier to make and operate.

Gas flux computations based on the EA concept or the REA concept and based on data collected using a gas flux measurement system (e.g., system 100 in FIG. 1) are implemented in various embodiments. In certain embodiments, rather than collecting gas, C (or Q), into actual bags using actual high-speed sampling devices, a high-speed time series of wind speed measurements (W) is used to determine when updrafts or downdrafts have occurred and a low-speed time series of gas concentration or content measurements are used to determine the gas content during the particular updraft or downdraft periods.

Using the surface renewal (SR) method, for example, allows calculations of fluxes from ramps in gas concentrations or temperature measurements, without the need for vertical wind speed measurements, and in some cases without the need for any wind speed measurements.

FIG. 1 illustrates a gas flux measurement system 100 according to an embodiment. Gas Flux measurement system 100 includes a wind speed measurement device 110 and a gas content measurement device 120. A control module 130 is coupled with the wind speed measurement device 110 and the gas content measurement device 120. In certain aspects, control module 130 includes an intelligence module such as one or more processors or a computer system, and associated memory, that is configured to provide control signals to any device or component in system 100, including for example wind speed measurement device 110 and gas content measurement device 120, as necessary, and to receive data and other signals from the component(s), e.g., wind speed measurement device 110 and gas content measurement device 120. In certain aspects, the wind speed measurement device 120 incudes a device capable of measuring vertical wind speed, or horizontal wind speed, or both vertical wind speed and horizontal wind speed. In certain aspects, control module 130 is configured with logic to perform the data collection and flux calculation processing functionality based on signals received from the various measurement components, e.g., wind speed measuring device 110 and the gas content measurement device 120, as described herein. It should be understood that the control module 130 could be a separate device as shown or could be integrated with a measurement device, e.g., one of wind speed measurement device 110 or gas content measurement device 120, or other system component. It should also be understood that control module 130 may be configured to merely collect and store the data and that the collected data may be transmitted to, sent to, or otherwise provided to a separate system that implements the data processing and flux computation functionality described herein.

In one embodiment, wind speed measurement device 110 includes an anemometer for measuring vertical wind speed, e.g., at a sampling rate of about 5 Hz or greater. However, wind speed measurement device 110 may include any device suitable for measuring wind speed at a desired sampling rate. Other useful wind speed measuring devices include hot film anemometers, ionization anemometers, laser anemometers, scintillometers, sonar devices and others. Gas content measurement device 120 includes any device suitable for measuring gas content of a desired target gas at a desired sampling rate, e.g., a sampling rate of between about 0.001 Hz to about 20 Hz or more. For example, in one embodiment, the gas content measurement device 120 includes a gas analyzer (e.g., an open-path or a closed-path gas analyzer). Useful gas analyzers include NDIR based analyzers, laser based analyzers, chemical-based analyzers, etc. Specific useful gas analyzers include the LI-7200 gas analyzer and the LI-7500 gas analyzer, both from LI-COR Biosciences, Lincoln, Nebr. U.S. Pat. Nos. 6,317,212, 6,369,387, 8,125,626 and 8,130,379, which are each hereby incorporated by reference in its entirety, disclose various useful features of open and closed path gas analyzers. In certain aspects, the time response of the gas content measurement device and the sampling rate need not be the same or similar. For example, a slow device, e.g., with time response of 1 Hz or less may be used and this slow signal may be sampled at a faster rate, e.g., at 20 Hz, however, the effective sampling rate is still limited by the slow device at 1 Hz or less.

Other measurement devices (not shown) in system 100 may include a temperature sensor, a humidity sensor, a gas sensor, a wind sensor, a pressure sensor, etc.

It should be appreciated that in some embodiments, a certain measurement device may not be present in a system and/or a certain measurement device or devices may not be operable for a certain time period. Regardless, the present embodiments compensate for such configurations and/or such inoperable equipment as various flux determination methods may not require certain equipment to be present or operational. For example, the present embodiments enable a station or system to operate effectively; if environmental or system conditions or station operation conditions are not viable for one or more methods, one or more other methods may still work and could be used by the station to determine useful gas flux values. For example, in the case where a wind speed measurement device may not be present in the system, or if present, may not be operable to measure wind speed, gas flux values may still be determined. The system can operate without wind speed data (e.g., without vertical wind speed data and/or horizontal wind speed data): one or more of a surface renewal (SR), a gradient flux calculation, a resistance flux calculation, an aerodynamic flux calculation, a Bowen ratio flux calculation, and an integrated horizontal flux calculation algorithm may be used as these methods do not need vertical wind speed. Some of these methods only need horizontal wind speed and others do not need any kind of wind speed.

Hence, as an example, the wind speed measurement device 110 (e.g., anemometer) on the station may be missing from the system entirely, or be inoperable, yet the station can still provide reasonable fluxes. And if there was enough time when the anemometer was operational, and other methods were tuned using the EC method, as an example, the station is likely to provide quite a good data for a long period of time, e.g., weeks, without any anemometer.

As another example, the system can also operate without a gas analyzer (or with a broken gas analyzer) and output correct sensible heat flux and momentum flux, computed by several methods, if the anemometer is operational. The correct sensible heat flux and momentum flux are valuable by themselves even when the gas fluxes cannot be computed.

As another example, the system can also operate without any anemometer or any gas analyzer (or with both broken) and output correct sensible heat flux, computed by several methods, if temperature measurements are available from a temperature sensor. The correct sensible heat flux is valuable by itself even when gas fluxes cannot be computed.

As another example, the system can also operate without any anemometer or gas analyzer (or with both broken) and output correct latent heat flux (water vapor flux) computed by several methods, if relative humidity (RH) measurements are available from a humidity sensor. The correct latent heat flux is very valuable by itself even when other gas fluxes cannot be computed.

Figure 2:
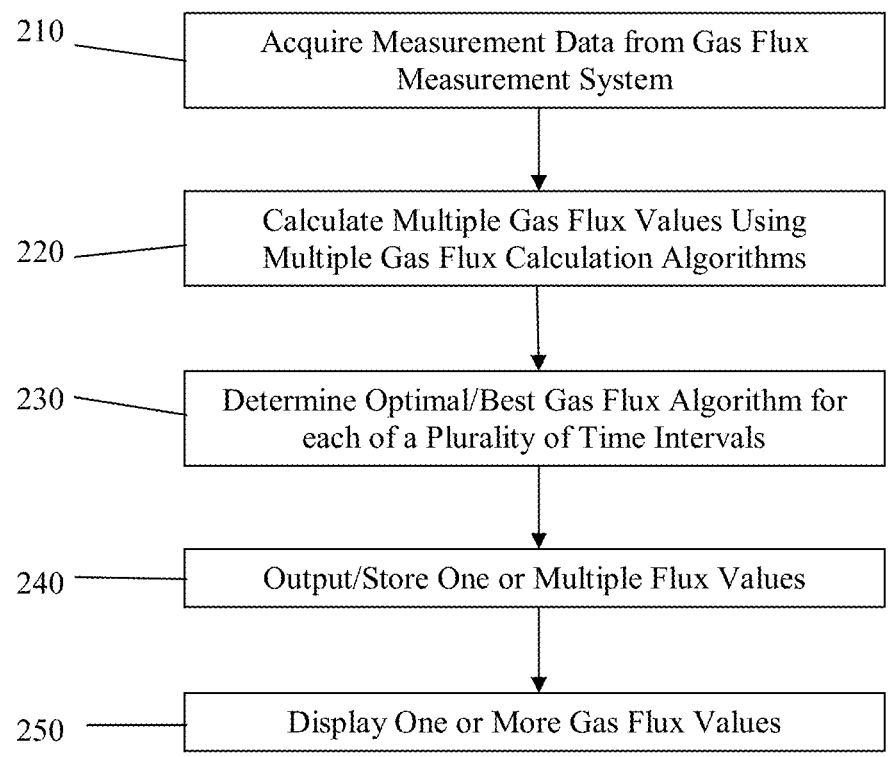
FIG. 2 illustrates a method of measuring gas flux according to an embodiment.

FIG. 2 illustrates a method 200 of measuring gas flux according to an embodiment. Method 200 may be implemented in a component of a gas flux measurement system, e.g., system 100) or is a stand-alone device or system remote from the gas flux measurement system from which the various measurement data is acquired. At step 210, data is obtained or acquired using one or more measurement components of a gas flux measurement system (e.g., system 100). For example, in an embodiment including a wind speed measurement device and a gas analyzer, step 210 may include obtaining wind speed data using the wind speed measurement device and also obtaining gas content data using the gas analyzer. The wind speed data may include a plurality a wind speed measurements (vertical and/or horizontal wind speed measurements) measured by the wind speed measurement device over a period of time at a sampling rate of the wind speed measurement device. Similarly, the gas content data may include a plurality of gas content measurements measured by the gas analyzer over the same period of time, or over a substantially similar period of time, at a sampling rate of the gas analyzer. For example, the period of time during which measurements are taken by both the wind speed measurement device and gas analyzer and/or other environmental parameter detection devices, may be greater than the actual time period during which measurements are actually taken by either device, such that if/when there is a discrepancy or difference of up to a few or several minutes between when the wind speed measurement device measures and the gas analyzer measures, the actual measurements taken fall within the substantially the same "period of time". In this manner, any flux calculation algorithms to be used on the acquired data may use values from slightly different shifted timings, all of which may be considered to be within the same "period of time." Further, "the substantially same period of time" during which measurements are taken by different devices encompasses the situation where one shifts the measurement time interval of one device by a few seconds or even a few minutes (e.g., <10 min for 60 min period; <1 min for 5 min period) relative to the measurement time interval of another device.

At step 220, a plurality of different gas flux values are calculated using the acquired data, e.g., data acquired during the period of time measurements were taken by the various measurement instruments of the system, using a corresponding plurality of different flux calculation algorithms available in the system. Each of the different flux calculation algorithms may use one or both of the wind speed data and the gas content data, and/or other environmental measurement data, to calculate gas flux values for a plurality of sub-periods or intervals of the period of time during which measurements were taken. The plurality of different flux calculation algorithms available in the system may include one or more of an eddy covariance (EC) flux calculation algorithm, an eddy accumulation (EA) flux calculation algorithm, a relaxed eddy accumulation (REA) flux calculation algorithm, a surface renewal (SR) flux calculation algorithm, a gradient flux calculation algorithm, a resistance flux calculation algorithm, an aerodynamic flux calculation algorithm, a Bowen ratio flux calculation algorithm, an integrated horizontal flux calculation algorithm and other calculation algorithms as would be apparent to one skilled in the art.

At step 230, for each of the plurality of sub-periods or intervals of the period of time, an optimal flux calculation algorithm is determined from among the plurality of different flux calculation algorithm used to calculate flux values based on one or more quality indicators. For example, in an embodiment, a primary flux calculation algorithm is determined as the flux calculation algorithm having the most number of sub-periods being determined as the optimal flux calculation algorithm. In an embodiment, one or more of the other flux calculation algorithms not determined as the primary flux calculation algorithm for certain sub-period may be tuned or calibrated. For example, one of the other flux calculation algorithms not determined as the primary flux calculation algorithm for a certain time period may be tuned based on the computed flux value of the primary flux calculation algorithm during that sub-period.

In an embodiment, for any sub-period during which the primary flux calculation algorithm either is unable to calculate a gas flux value, or is determined as not being the optimal flux calculation algorithm, the method further includes using the computed flux value of the tuned or calibrated flux calculation algorithm for that sub-period.

The sub-periods of time or intervals may be automatically determined by the system, e.g., based on one or more sampling rates of the instruments, or they may be determined based on user input. The quality indicators may include one or more environmental parameters and/or one or more system parameters.

In certain embodiments, the environmental parameters are derived from information including one or more of the following:
date information;
coordinate location information
study site information;
topography information;
measurement height information;
canopy height information;
atmospheric conditions information;
weather conditions information;
soil conditions information;
canopy conditions information, e.g., leaf-on or leaf-off period;
snow/ice cover information; etc.;
and
information on interaction of some of the data with some of the environmental parameters (for example wind direction vs topography features at a specific site at specific time).

In certain embodiments, each of the system parameters are derived from information including one or more of the following:
instrument configuration information;
instrument operation information;
instrument diagnostic information;
instrument performance degradation information;
data reliability/quality information;
calculations reliability/quality information; etc.;
and
information on interaction of some of the data with some of the system parameters (for example, canopy height and measurement height vs system frequency response at a specific site and specific time: for example, if the measurement height was 1.5 m and corn has overtime grown to 1 m, the EC method may no longer be desired as the primary method).

At step 240, one or more optimal flux calculation values are output and/or stored to a memory. For example, for each of the plurality of sub-periods or intervals of time, one or more optimal flux calculation values corresponding to the optimal flux calculation algorithm for the sub-period are output or stored.

At optional step 250, one or more of the optimal/best flux values may be displayed using a display device, such as a computer display screen running a user interface program configured to visually display the flux values and/or other related information. For example, in an embodiment, the one or more optimal flux values determined for each of the plurality of sub-periods may be displayed. In another embodiment, the flux values computed by a primary flux calculation algorithm may be displayed, with the primary flux calculation algorithm being determined as the flux calculation algorithm having the most number of sub-periods being determined as the optimal flux calculation algorithm. In another embodiment, the gas flux values for each of the plurality of sub-periods computed by each of the plurality of different flux calculation algorithms may be displayed.

In certain embodiments, some or all of the assigned quality flags or quality indicators for each method of calculation may be displayed, providing the user with all possible flux outputs and quality indicators for further analysis. The station may recommend the best value or values but also may provide actionable information on all possible values determined by various methods for a given time period.

Advantageously, the various embodiments enable to accommodate future yet-to-be invented algorithms for more diverse intelligent selection of the best flux value depending on the site, weather and instrument conditions. For example, someone may come up with, or resurrect, yet another flux calculation algorithm or invent an entire new flux method; the present embodiments can accommodate such new methods.

In certain embodiments, the system may output values from all the used methods as a cloud of points distributed around the perceived best flux value. For example, the system may output values from all the used methods (best and not so good) as a cloud of points to arrive to the perceived best flux value.

In certain embodiments, the system may implement machine-learning algorithms and may effectively become an intelligent autonomous real-time flux measurement system.

In certain embodiments, the system computes one or more fluxes by several (two or more) methods, and the calculations may be done automatically, in near-real-time, or real-time. The calculations can be performed at the flux measurements station, or they can be performed remotely using a cloud/server paradigm, with an interconnection to the station continuously or intermittently, or calculations can be divided among different entities, e.g., the station may perform one or more calculations and a server may perform one or more calculations simultaneously or at a different point in time using the same data set, or data from the same data set.

In certain embodiments, the system automatically evaluates and identifies what is the most reliable method for a given period (e.g., 5-240 min period) depending on set conditions.

In certain embodiments, the station may select the period or periods when the best method has high quality performance and then uses these period(s) to tune and calibrate secondary methods. The station uses the tuned secondary methods (fine-tuned by a primary method, or as is) to gap-fill the periods when the primary methods had low-quality performance In certain embodiments, the station may provide or output some or all of the multitude of results from all used methods, including descriptive statistics and cumulative values performance.

In some embodiments, the station may produce or output the most continuous set of the best estimates of the flux regardless of the method(s) used.

Figure 3:
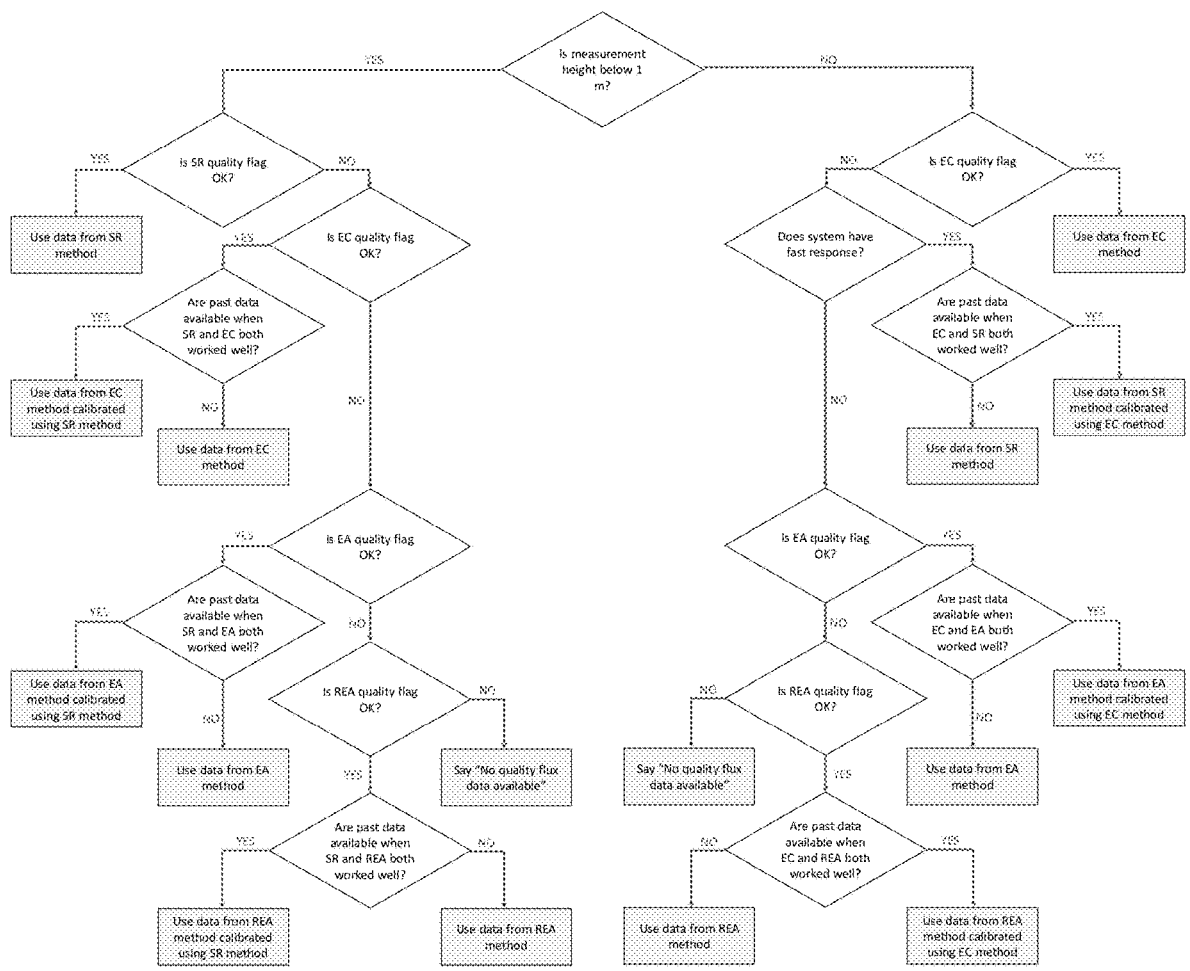
FIG. 3 illustrates an example embodiment of a multi-method flux station decision tree for determining which of multiple measurement methods may provide the optimal or best flux value(s) for a specific station or system configuration and performance, weather conditions and measurement time period.

FIG. 3 illustrates an example embodiment of a multi-method flux station decision tree for determining which of multiple measurement methods may provide the optimal or best flux value(s) for a specific station or system configuration and performance, weather conditions and measurement time period. The decision tree may be implemented using data from multiple measurement devices according to an embodiment. One skilled in the art will understand that the decision tree illustrated in FIG. 3 is but one of many possible decision tress that may be implemented based on the teachings herein.

In this example, it is assumed for the sake of simplicity that there are 4 available methods of flux calculations: EC, SR, 1 EA and 1 REA. Additional available flux calculation methods and additional criteria will make the decision tree more elaborate and complex but will also lead to more choices and to better decisions.

FIG. 4 shows one example of an algorithm (e.g., conditions and parameters) than can be used to determine primary and secondary methods according to an embodiment. As shown, the system uses 9 different methods simultaneously and uses data from the same gas analyzer and then selects the primary, secondary and other methods computed by the system logic.

Example of an Operation is a Corn Field

The example of applying of the multi-method algorithm at the station placed in a corn-planted field 3 m from soil surface, and using closed-path gas analyzer:

Spring Operation:
Initial install
Intake filter is clean
Canopy height is zero
Measurement height is 3 m above ground
System frequency response is 7 Hz
Frequency correction multiplier in the middle of the day is 1.1
Primary methods are EC and EC-RR
Secondary method is SR
Tertiary method is EA
Next method is =REA Fall Operation:
Several months in the field
Intake filter is dirty
Canopy height is 2.2 m
Measurement height is 0.8 m above ground
System frequency response is 5 Hz
Frequency correction multiplier in the middle of the day is 1.4
Primary method is SR
Secondary methods are EC and EC-RR
Tertiary method is EA
Next method is REA
Confident high-quality SR periods (with high quality QC flags) can be used to calibrate EC, EA, REA methods, then EC, EA, REA methods can be used to calibrate SR method and gap-fill poor SR periods (for example, SR algorithm can't find ramp fit)
Confident high-quality EC periods (e.g. with high quality QC flags) can be used to calibrate SR, EA, REA methods, then SR, EA, REA methods can be used to gap-fill poor EC periods (for example, sonic during anemometer malfunction).

Winter Operation:
Infrequent visits
Intake filters is frozen
Canopy height is zero
Measurement height is 3 m above ground
System frequency response is 0.5 Hz
Frequency correction multiplier in the middle of the day is over 2.0 or can't be computed
Primary methods are EA and REA
Secondary methods are EC and EC-RR
Tertiary method is SR
Confident EA/REA periods (with high quality flags) can be used to calibrate EC method, then EC methods can be used to gap-fill poor EA/REA periods (for example, EA algorithm can't resolve the bins)

Regardless of conditions of the weather or the measurement system, the station will report the best available estimates/calculations of the flux, with other fluxes also recorded and flagged to indicate lack of reliability. This is just one simple example demonstrating how the station works in an embodiment: much more advanced logic can be built depending on the number of methods involved.

Figure 5:
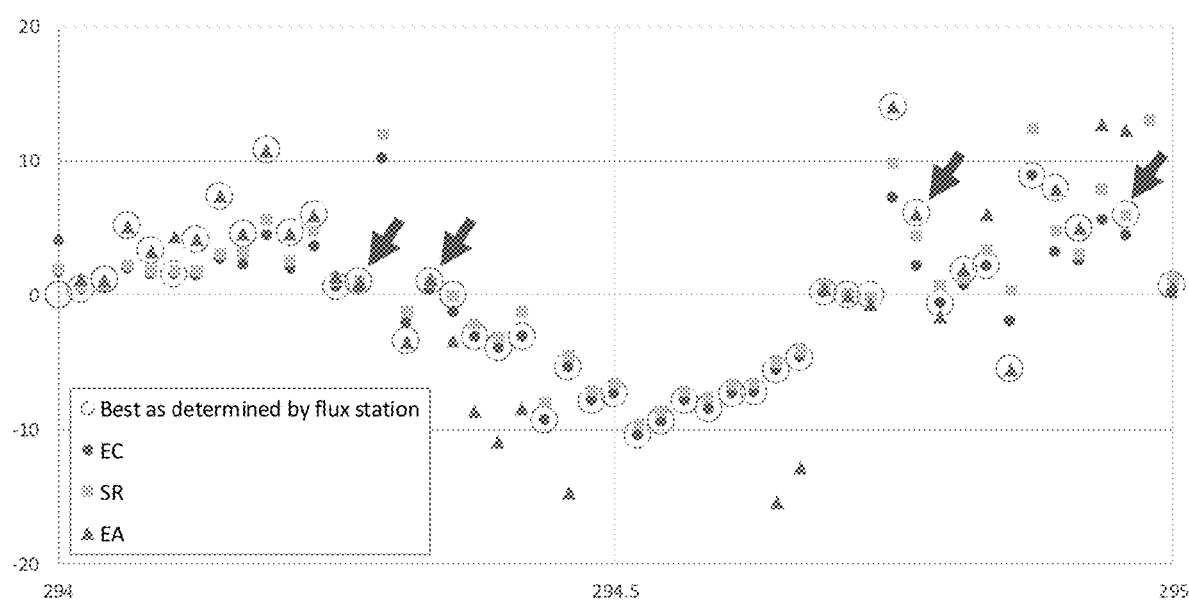
FIG. 5 illustrates selection of the best possible hourly flux according to an embodiment.

FIG. 5 illustrates and example data display using 1 year of actual EC data, alongside simulated SR and EA data, taken from the LERS (LI-COR Experimental Research Station (LERS) is a permanent multi-purpose experimental field facility in Lincoln, Nebr. used for development and testing of new instrumentation and methods for environmental research and monitoring). Several conditions were set to make each of the methods perform poorly. For example, EC did not perform well at low winds and with low flow rates, SR did not perform well in highly unstable atmosphere, and EA did not perform well with small variance in w. The algorithm was made to determine periods when each method had good and bad performance. The best flux was selected based on the available good fluxes. When one method did not have good performance, the regression was used to recover such a bad period using other methods if these had good performance during the same time.

Again, this is just an example demonstrating how the station works in an embodiment: much more advanced logic can be built depending on the data available and number of methods involved.

As shown in FIG. 5, the best possible hourly flux is selected. For given conditions at LERS, EC is the best possible flux most of the time. However, SR and EA are also selected during the hours when EC is not credible. One variation of the above approach is to use not the original fluxes from SR and EA methods, but rather adjusted fluxes from SR and EA methods based on the relationship with EC during common good periods.

Figure 6:
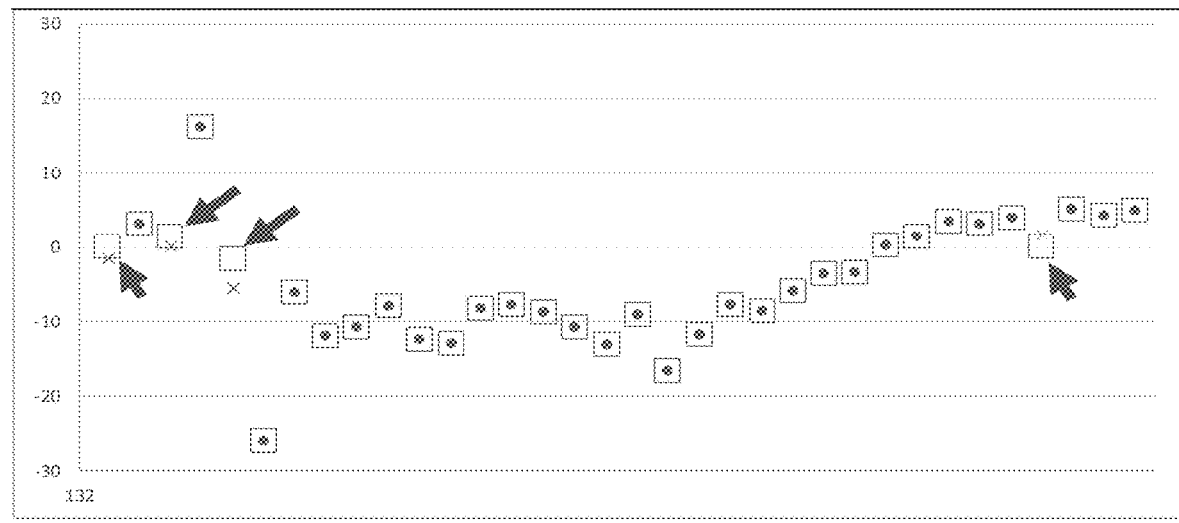
FIG. 6 illustrates results of an algorithm according to an embodiment recovering hourly fluxes from one method (EC in this example) based on the relationship developed with other available methods when those methods performed well.

FIG. 6 illustrates the algorithm recovering hourly fluxes from one method (EC in this example) based on the relationship developed with other available methods when those methods performed well.

Figure 7:
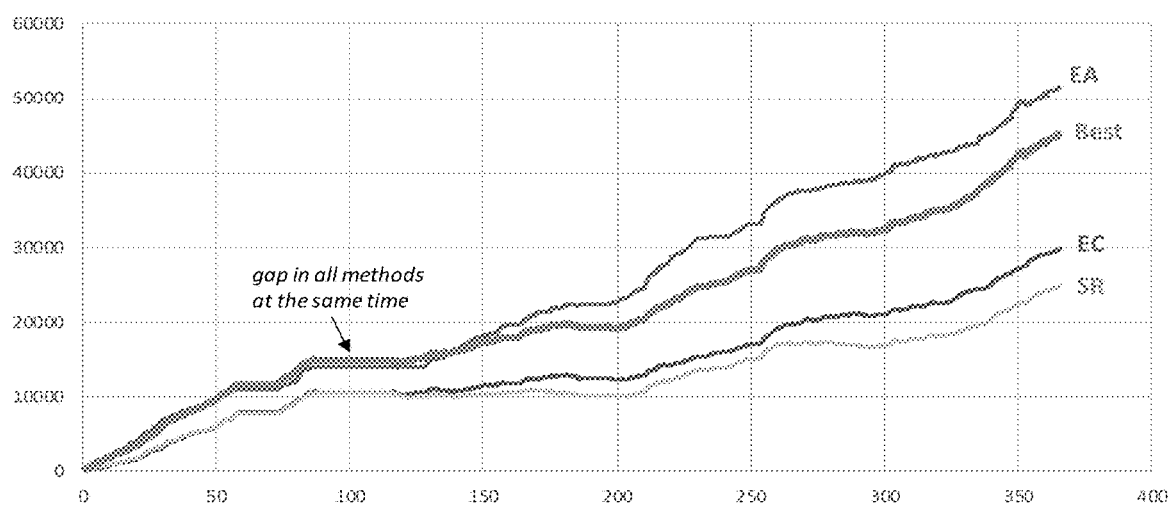
FIG. 7 illustrates the best estimate of yearly carbon budgets measured by an automated multi-flux station according to an embodiment

FIG. 7 illustrates the best estimate of yearly carbon budgets measured by an automated multi-flux station according to an embodiment. EC had most hours with best quality credible data, but also had a lot of missing data nearly every night. SR had less missing data but was biased lower than realistic estimates. EA also had less missing data but was biased higher than the realistic estimates. The best fluxes line represents mostly EC fluxes gap-filled using regressions with SR fluxes when available, and then with EA fluxes when available. There was one month-long period with no good methods available: this period could be recovered using a gap-fill process; gap-filling of long gaps can also be implemented in an automated fashion.

It should be appreciated that the gas flux determination processes described herein may be implemented in processor executable code running on one or more processors. The code includes instructions for controlling the processor(s) to implement various aspects and steps of the gas flux determination processes. The code is typically stored on a hard disk, RAM or portable medium such as a CD, DVD, etc. The processor(s) may be implemented in a control module of a gas flux measurement system, or in a different component of the system such as gas analyzer having one or more processors executing instructions stored in a memory unit coupled to the processor(s). The processor(s) may be part of a separate system directly or indirectly coupled with the gas flux measurement system. Code including such instructions may be downloaded to the system or gas analyzer memory unit over a network connection or direct connection to a code source or using a portable, non-transitory computer-readable or processor-readable medium as is well known.

One skilled in the art should appreciate that the processes of the present invention can be coded using any of a variety of programming languages such as C, C++, C#, Fortran, VisualBasic, etc., as well as applications such as Mathematica® which provide pre-packaged routines, functions and procedures useful for data visualization and analysis. Another example of the latter is MATLAB®.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Exemplary embodiments are described herein. Variations of those exemplary embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of measuring gas flux, the method comprising:
   obtaining wind speed data, the wind speed data including a plurality of wind speed measurements measured by a wind speed measurement device over a period of time at a sampling rate of the wind speed measurement device;
   obtaining gas content data, the gas content data including a plurality of gas content measurements measured by a gas analyzer over said period of time at a sampling rate of the gas analyzer;
   computing a plurality of different gas flux values for said period of time using a corresponding plurality of different flux calculation algorithms, wherein each of the plurality of different flux calculation algorithms uses one or both of the wind speed data and the gas content data to calculate gas flux values for a plurality of sub-periods of said period of time;
   for each of the plurality of sub-periods of said period of time, determining an optimal flux calculation algorithm of the plurality of different flux calculation algorithms based on one or more quality indicators; and
   outputting or storing, for each of the plurality of sub-periods, one or more optimal flux calculation values corresponding to the optimal flux calculation algorithm for the sub-period.

2. The method of claim 1, further including displaying one or more of:
   the one or more optimal flux values determined for each of the plurality of sub-periods;

the flux values computed by a primary flux calculation algorithm, wherein the primary flux calculation algorithm is the flux calculation algorithm having the most number of sub-periods being determined as the optimal flux calculation algorithm; and the gas flux values for each of the plurality of sub-periods computed by each of the plurality of different flux calculation algorithms.

3. The method of claim 1, wherein the plurality of different flux calculation algorithms include one or more of an eddy covariance (EC) flux calculation algorithm, an eddy accumulation (EA) flux calculation algorithm, a relaxed eddy accumulation (REA) flux calculation algorithm, a surface renewal (SR) flux calculation algorithm, a gradient flux calculation algorithm, a resistance flux calculation algorithm, an aerodynamic flux calculation algorithm, a Bowen ratio flux calculation algorithm, and an integrated horizontal flux calculation algorithm.

4. The method of claim 1, wherein the one or more quality indicators include parameters selected from the group consisting of environmental parameters and system parameters.

5. The method of claim 4, wherein the environmental parameters are derived from information including one or more of the following:
date information;
coordinate location information
study site information;
topography information;
measurement height information;
canopy height information;
atmospheric conditions information;
weather conditions information;
soil conditions information;
canopy conditions information;
snow/ice cover information;
and
information on interaction of one or more system parameters with one or more environmental parameters
and
wherein each of the system parameters are derived from information including one or more of the following:
instrument configuration information;
instrument operation information;
instrument diagnostic information;
instrument performance degradation information;
data reliability/quality information;
calculations reliability/quality information;
and
information on interaction of one or more environmental parameters with one or more system parameters.

6. The method of claim 1, further including:
determining a primary flux calculation algorithm as the flux calculation algorithm having the most number of sub-periods being determined as the optimal flux calculation algorithm; and
for a first sub-period, tuning or calibrating one of the other flux calculation algorithms not determined as the primary flux calculation algorithm based on the computed flux value of the primary flux calculation algorithm for the first sub-period.

7. The method of claim 6, wherein for a second sub-period, the primary flux calculation algorithm either is unable to calculate a gas flux value, or is determined as not being the optimal flux calculation algorithm,
wherein the method further includes using the computed flux value of the tuned or calibrated flux calculation algorithm for the second sub-period.

8. The method of claim 1, further including obtaining temperature data, the temperature data including a plurality of temperature measurements measured by a temperature measuring device over said period of time, and wherein at least one of the plurality of different flux calculations uses the temperature data when calculating gas flux values for the plurality of sub-periods.

9. The method of claim 1, wherein the sampling rate of the wind speed measurement device is different than the sampling rate of the gas analyzer.

10. The method of claim 1, wherein the steps of computing, determining and outputting or storing are performed automatically in real time as the wind speed data and the gas content data are being obtained.

11. The method of claim 1, further including obtaining temperature data, the temperature data including a plurality of temperature measurements measured by a temperature measuring device over said period of time, and wherein at least one of the plurality of different flux calculations uses the temperature data and the wind speed data to calculate sensible heat flux values for the plurality of sub-periods.

12. The method of claim 1, further including obtaining temperature data, the temperature data including a plurality of temperature measurements measured by a temperature measuring device over said period of time, and wherein at least one of the plurality of different flux calculations uses the temperature data to calculate sensible heat flux values for the plurality of sub-periods.

13. The method of claim 1, further including obtaining relative humidity data, the relative humidity data including a plurality of humidity measurements measured by a relative humidity measuring device over said period of time, and wherein at least one of the plurality of different flux calculations uses the relative humidity data to calculate latent heat flux values for the plurality of sub-periods.

14. The method of claim 1, further including obtaining gas concentration data, including a plurality of gas concentration measurements measured by a gas concentration measuring device over said period of time, and wherein at least one of the plurality of different flux calculations uses the gas concentration data to calculate gas flux values for the plurality of sub-periods.

15. The method of claim 1, further comprising assigning a quality value or quality indicator to each of the plurality of different flux calculation algorithms used when computing the plurality of different gas flux values for said period of time.

16. A system for measuring gas flux, the system comprising:
a wind speed measurement device configured to obtain wind speed data including a plurality of wind speed measurements obtained over a period of time at a first sampling rate;
a gas analyzer configured to obtain gas content data including a plurality of gas content measurements obtained over said period of time at a second sampling rate; and
an intelligence module adapted to receive the wind speed data and the gas content data, wherein the intelligence module including a processor configured to automatically:
compute a plurality of different gas flux values for said period of time using a corresponding plurality of different flux calculation algorithms, wherein each of the plurality of different flux calculation algorithms uses one or both of the wind speed data and the gas content data to calculate gas flux values for a plurality of sub-periods of said period of time;

for each of the plurality of sub-periods of said period of time, determine an optimal flux calculation algorithm of the plurality of different flux calculation algorithms based on one or more quality indicators; and output or store, for each of the plurality of sub-periods, one or more optimal flux calculation values corresponding to the optimal flux calculation algorithm for the sub-period.

17. The system of claim 16, wherein the intelligence module is implemented in a device separate from the wind speed measurement device and the gas analyzer.

18. The system of claim 16, wherein the steps of computing, determining and outputting or storing are performed automatically in real time as the wind speed data and the gas content data are being obtained.

19. A non-transitory, computer-readable medium that stores code, which when executed by one or more processors causes the one or more processors to implement a method of:

obtaining wind speed data, including a plurality wind speed measurements measured by a wind speed measurement device over a period of time at a sampling rate of the wind speed measurement device;

obtaining gas content data, the gas content data including a plurality of gas content measurements measured by a gas analyzer over said period of time at a sampling rate of the gas analyzer;

computing a plurality of different gas flux values for said period of time using a corresponding plurality of different flux calculation algorithms, wherein each of the plurality of different flux calculation algorithms uses one or both of the wind speed data and the gas content data to calculate gas flux values for a plurality of sub-periods of said period of time;

for each of the plurality of sub-periods of said period of time, determining an optimal flux calculation algorithm of the plurality of different flux calculation algorithms based on one or more quality indicators; and outputting or storing, for each of the plurality of sub-periods, one or more optimal flux calculation values corresponding to the optimal flux calculation algorithm for the sub-period.

20. A method of measuring gas flux, the method comprising:

obtaining one or more of wind speed data, gas content data, temperature data and humidity data over a period of time;

computing a plurality of different gas flux values for said period of time using a corresponding plurality of different flux calculation algorithms, wherein each of the plurality of different flux calculation algorithms uses one, some or all of the wind speed data, the gas content data, the temperature data and the humidity data to calculate gas flux values for one or a plurality of sub-periods of said period of time;

for each of the one or the plurality of sub-periods of said period of time, determining an optimal flux calculation algorithm of the plurality of different flux calculation algorithms based on one or more quality indicators; and outputting or storing, for each of the plurality of sub-periods, one or more optimal flux calculation values corresponding to the optimal flux calculation algorithm for the sub-period.

\* \* \* \* \*